US005773287A

United States Patent [19]
Binder

[11] Patent Number: 5,773,287
[45] Date of Patent: Jun. 30, 1998

[54] INCUBATOR

[76] Inventor: Peter Michael Binder, Säntisstrasse 74A, D—88662 Überlingen, Germany

[21] Appl. No.: 538,020

[22] Filed: Oct. 2, 1995

[30] Foreign Application Priority Data

Nov. 19, 1994 [DE] Germany .......................... 44 41 250.9

[51] Int. Cl.$^6$ .................................................. C12M 3/00
[52] U.S. Cl. ........................ 435/303.1; 435/809; 119/6.6; 219/385; 219/407; 312/31.2; 312/209; 422/104
[58] Field of Search ................................ 435/303.1, 809; 219/392, 393, 385, 401, 407; 312/31.2, 209; 422/104; 119/6.6

[56] References Cited

U.S. PATENT DOCUMENTS 4,923,816  5/1990  Heeg et al. .............................. 435/284

OTHER PUBLICATIONS

Patent Abstracts of Japan, vol. 17/No. 678 (Dec. 13, 1993); English abstract for Japanese Patent Appln. No. 4–73447.

*Primary Examiner*—David A. Redding
*Attorney, Agent, or Firm*—Foley, Hoag & Eliot LLP; Sayoko Blodgett-Ford; Donald W. Muirhead

[57] ABSTRACT

An aeration incubator achieves a high atmospheric humidity in the interior working space of the incubator by placing a heated water tub in the working space. In order to avoid condensation on the walls of the incubator tank, a condensate tub is also placed in the working space. The condensate tub is maintained at a temperature which is slightly lower than the temperature of the working space. The condensate tub produces a defined coldest location in the working space, so that condensation occurs primarily in the condensate tub.

32 Claims, 1 Drawing Sheet

INCUBATOR

TECHNICAL FIELD

This invention relates to the field of incubators and more particularly to the field of incubators for incubation of cells and tissue cultures in vitro.

BACKGROUND OF THE INVENTION

Certain types of incubators, such as those disclosed in DE 38 15 528 C1, for example, provide incubation of cell and tissue cultures in vitro. Conditions in the interior working space of the incubator must be regulated and maintained in order to replicate as precisely as possible the physiological conditions of the organism from which the cells originate. In order to maintain the temperature of the working space atmosphere as steadily as possible at the temperature of the animal from which the cells came (e.g., 37° C. for human cells), all of the walls of the tank that enclose the incubator working space can be heated by a hot air mantle that envelopes the outside of the walls of the incubator working space.

In order to prevent drying of the cell and tissue cultures, the humidity of the incubator working space atmosphere is maintained as high as possible, preferably above 95% relative atmospheric humidity. One type of incubator that can be used in this field is an aeration incubator, in which a precisely regulated concentration of $CO_2$ is maintained in the working space atmosphere. Regulation of the $CO_2$ controls the ph-value of a buffer solution (such as sodium bicarbonate solution) in which the cultures can be embedded.

Maintaining the high humidity within the working space causes unwanted moisture from the atmosphere of the working space to easily condense on the walls thereof when a portion of the walls falls below the dew point (the temperature at which vapor begins to condense). This often occurs in the corners and at the edges of the tank, where flow conditions of the hot air mantle create uneven heating of the walls. Unwanted organisms, such as fungi, bacteria, or viruses, can easily grow in the condensation because the working-space conditions that are optimal for incubation of cell and tissue cultures are also favorable to maximal growth of these contaminating organisms. The growth of such organisms can be a serious problem. The unwanted organisms can contaminate the cultivated cell cultures themselves whereby research results obtained at great expenditure can be endangered. In addition, growth of the unwanted organisms necessitates time-consuming and costly cleaning of the incubator.

DE 38 15 528 C1 discloses an aeration incubator in which a high relative atmospheric humidity of up to 97% can be achieved by using a water bath placed on the floor of the working space and heated by heaters attached to an exterior portion of the floor. The water bath is preferably maintained at a temperature which is slightly higher than the temperature of the working space atmosphere. However, this system suffers from the problem discussed above wherein the atmospheric humidity can condense on the relatively poorly heated and therefore colder back wall of the tank. Depending on the operating conditions, the entire back wall can get wet. In addition, this high humidity in the working space of the incubator is regenerated whenever the door of the incubator is opened.

It is therefore desirable to cost effectively improve incubator humidification in such a way that despite a high atmospheric humidity, and the rapid regeneration of this humidity after opening of the incubator door, the working space remains reliably dry and free of condensation.

SUMMARY OF THE INVENTION

The present invention takes advantage of the fact that inside a closed volume in which water is located, the atmospheric humidity varies according to the saturation vapor pressure, which corresponds to the temperature of the coldest location of the volume. If the water vapor pressure rises above the saturation vapor pressure, which varies according to the coldest temperature, the water vapor will condense at this coldest point until the atmospheric humidity corresponds to the saturation vapor pressure of this coldest temperature.

According to the present invention, the working space of an incubator includes a water tub arranged therein whose temperature is the same or slightly higher than the temperature of the working-space atmosphere and also includes a condensate tub arranged in the working space and maintained at a temperature which is lower than the temperature of the working space. The presence of the condensate tub creates a defined location of lowest temperature in the working space. The temperature of the condensate tub and the temperature of the condensate collected therein defines the saturation water pressure in the working space. The higher temperature of the water tub causes a constant evaporation of water out of the water tub, while the condensate tub provides a defined and controlled condensation location. By deliberately maintaining the condensate tub at a lower temperature, the temperature at other points of the working space, including the walls, tends to be higher than the temperature of the condensate tub even in the case of inevitable temperature fluctuations. Consequently, condensation tends to occur exclusively at the condensate tub while the rest of the working space remains relatively dry.

Because of the higher temperature of the water tub, water is constantly evaporating from the water tub while, on the other hand, a corresponding quantity of water vapor condenses in the condensate tub. Thus a steady state develops which results in high relative atmospheric humidity within the incubator. In addition, the higher temperature of the water tub is advantageous in that after opening of the door of the incubator and lowering the atmospheric humidity of the working space, the high atmospheric humidity steady state condition can be reestablished very quickly.

Both the water tub and the condensate tub can be arranged on the floor of the working space. The temperature of the water in these tubs can be regulated by heating and cooling the floor of the tank. The tubs can be formed in the tank's floor itself. However, since indentations in the floor for forming the water and condensate tubs can render cleaning of the working space more difficult, an interior-wall surface area which is as free of corners and edges as possible can be maintained by having the water tub and the condensate tub fashioned as basins that are placed independently on the floor of the tank. The water tub and the condensate tub can be formed in one piece out of a metal sheet, or can be fashioned as separate tubs. In addition, the tubs can be in heat-conducting contact with the bottom of the tank, so that heating and cooling from the exterior by way of the tank's floor can occur as efficiently as if the tubs were formed integral with the floor of the tank. The water and condensate tubs can be fashioned as bowls and can be, like the tank, made of high-grade or stainless steel to facilitate easy and thorough cleaning.

In order to maintain the water tub and the condensate tub at specified temperatures, heaters can be attached to an outside portion of the floor of the tank in a region near the water tub in order to heat water in the water tub. Since the metallic floor of the tank also conducts heat to the area on which the condensate tub is located, the lower temperature of the condensate tub can be regulated by cooling. Simple and low-cost cooling can be achieved by conducting cooler outside air past insulation of the incubator to an area of the tank's floor on which the condensate tub is located. Conveyance of air can be supported by a ventilator. Regulation of the temperature of the condensate tub is preferred. The temperature regulation can be provided by controlling output volume of the ventilator. In addition, controllable cooling of the conveyed surrounding air can be provided. Through these measures, cooling of the condensate tub is possible irrespective of the temperature of the outside air since the amount of air conveyed can be made to vary according to the temperature of the outside air.

In a preferred form of the invention, a large water tub is placed on the floor of the tank. The water tub has in the middle region thereof an opening into which the condensate tub is placed. Because the water tub and the condensate tub are fashioned as separate basins, thermal insulation between the water tub and the condensate tub is possible, so that the temperature difference between the two can be easily regulated and maintained. In addition, the water tub and the condensate tub can rest on the floor of the tank independently of each other, so that a good heat-conducting contact between the floor of the tank and the bottoms of the water tub and the condensate tub is assured, even if the floor of the tank is not completely flat.

Centrally arranging the condensate tub within the water tub has the further advantage in that the condensate tub, which is cooler and at which atmospheric humidity condenses, is located at a distance from the side walls, the back wall, and the door of the working space, thus minimizing the possibility that cooling of the condensate tub will lead to cooling and hence condensation deposits in parts of the tank. In a preferred embodiment, the condensate tub overlaps an edge of the surrounding water tub with a drip brim. Thus, liquid which condenses at the edge of the condensate tub cannot drip onto the floor of the tank, but rather, drips to the inside into the condensate tub or to the outside into the water tub. Even in the exceptional case that, with extended operation of the incubator, the condensate completely fills the condensate tub, excess condensate can drain by way of the drip brim into the water tub in order to be available for evaporation therein.

In a preferred embodiment, the incubator is made to work effectively and reliably by setting the temperature of the water supply to approximately the working-space temperature or slightly higher (several tenths °C.), thus causing high atmospheric humidity in the working-space in the steady state and causing a rapid humidification of the working space after opening the incubator door. In a preferred embodiment, the temperature of the condensate tub can be set to several °C., preferably 3° C., below the working space temperature. Thus, neither the working space temperature nor any location of the walls of the tank fall below the dew point of the water vapor pressure, since the dew point is defined by the temperature of the condensate tub. At operating temperature levels, the difference between the temperature of the water tub and the temperature of the condensate tub is sufficiently small to obtain a high relative atmospheric humidity, up to 96% in the steady state.

In the following, the invention is explained in more detail with the help of an exemplary embodiment depicted in the figures.

DETAILED DESCRIPTION OF THE PREFERRED EMBODIMENTS

Figure 1:
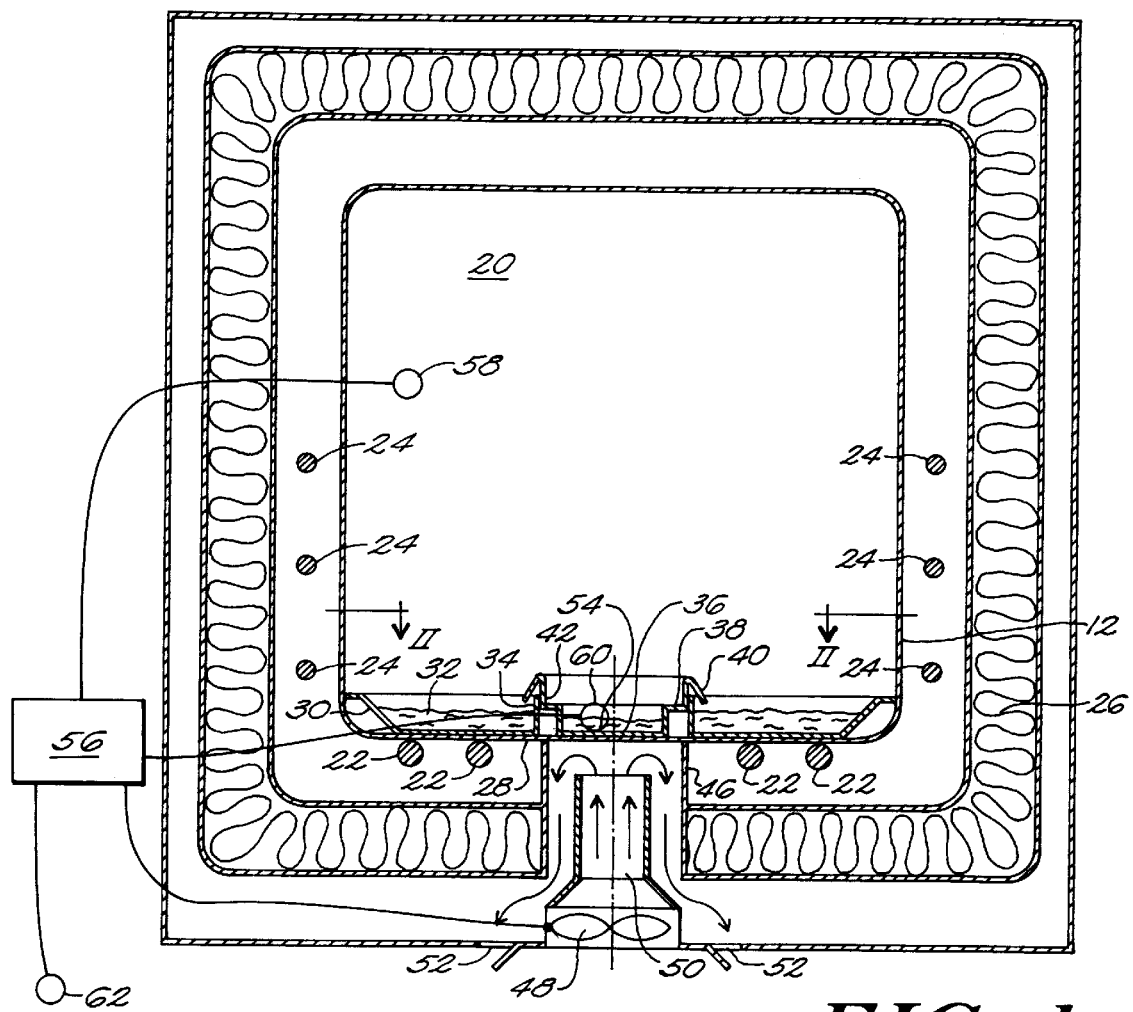
FIG. 1 schematically shows a vertical cross section of an aeration incubator in accordance with a line of intersection, I—I, in FIG. 2.
Figure 2:
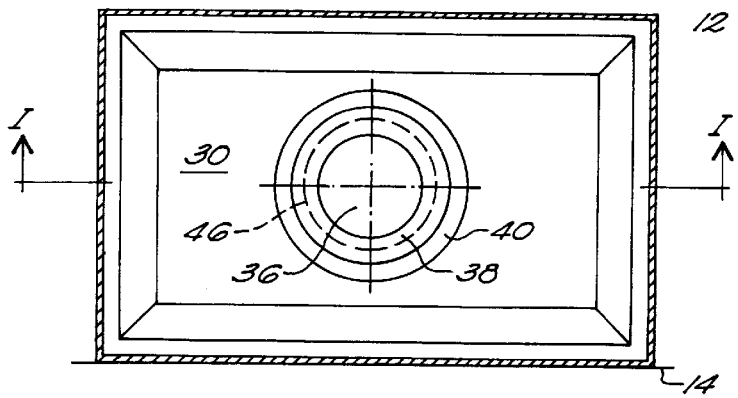
FIG. 2 schematically shows a horizontal cross section through a tank of the aeration incubator in accordance with a line of intersection, II—II, in FIG. 1.

Referring to FIG. 1, an aeration incubator includes a housing 10 having a tank 12 arranged therein. The tank 12 can be deep-drawn of high-grade steel and includes a floor 28. Walls of the tank 12 form a working space 20 of the incubator. An open front side of the tank 12 has a rim 14, which is furnished with a seal (not shown). A door (not shown) lines up with the seal for leakproof sealing of the tank 12. The tank 12 is surrounded on all sides thereof, except the open front side, by an outer tank 16. The outer tank 16 is located at a distance from the tank 12 so that a hot air mantle 18 can be formed between the tank 12 and the outer tank 16 in order to envelope walls of the tank 12. The hot air mantle 18 can be circulated by way of a hot air mantle ventilator (not shown). Heaters 24 are arranged within the hot air mantle 18 to regulate heating of the air circulated therein to an adjustable specified temperature. The heated air in the hot air mantle 18 heats the walls of the tank 12 to the specified temperature so that the walls of the tank 12 constantly maintain the temperature of the working space 20 at a specified level. The outer tank 16 is surrounded by insulation 26 in order to provide temperature stability for the hot air mantle 18.

A group of heaters 22 are arranged under the floor 28 of the tank 12 and are attached to an exterior portion of the floor 28 in heat conducting contact therewith. Other ones of the heaters 24 are arranged in lateral and the rear parts of the hot air mantle 18, at a particular distance from the tank 12 and the outer tank 16, so that the heaters 24 tend to only heat air which rises in the hot air mantle 18 without causing selective heating at certain points of the tank 12.

Two basin-shaped tubs, a water tub 30 and a condensate tub 36, also fashioned out of high-grade steel, can be placed on the floor 28 of the working space 20. The water tub 30 holds a water supply 32. The overall dimensions of the water tub 30 correspond essentially with the area of the floor 28, so that the water tub 30 covers nearly the entire floor 28 of the tank 12. The water supply 32, contained in the water tub 30, has a relatively large evaporation surface.

The water tub 30 can have a circular opening in the middle thereof which is surrounded by a vertical edge 34 of the water tub 30. The centrally located opening of the water tub 30 is used to hold the condensate tub 36. An edge 38 of the condensate tub 36 is higher than the vertical edge 34 of the water tub 30 and is flanged outward at an upper rim of the edge 38 in order to form a sloping drip brim 40. When the condensate tub 36 is placed in the centrally located opening of the water tub 30, the drip brim 40 overlaps the inner edge 34 of the water tub 30. Since the edge 38 of the condensate tub 36 is higher than the edge 34 of the water tub 30, the condensate tub 36 rests freely on the floor 28 of the tank 12, despite the overlapping drip brim 40. The edge 38 of the condensate tub 36 is shaped in such a way that an upper area 42 of the condensate tub 36 fits snugly against the inner edge 34 of the water tub 30. The region in which the upper area 42 and the inner edge 34 fit closely together functions as a vapor barrier, which prevents the atmosphere of the working-space 20, having a high atmospheric humidity, from coming into contact with the floor 28 of the tank 12. The heaters 22 are attached to an area of the floor 28 of the tank 12 in which the water tub 30 rests. Since both the floor 28 of the tank 12 and the floor of the water tub 30 are fashioned evenly, there is a large heat-conducting contact area between the floor 28 of the tank 12 and the floor of the water tub 30. Accordingly, the heaters 22 heat the water supply 32 in the water tub 30 by way of the floor 28 and the water tub 30.

No heaters are attached to the floor 28 in the area of the centrally located opening in the water tub 30. Instead, a shaft 46 is provided in this area. The shaft 46 is fastened below the floor 28 on an exterior portion thereof. The shaft 46 leads to the outside of the incubator through the hot air mantle 18, the heat insulation 26, and the casing 10. The shaft 46 has a cross-sectional area that essentially corresponds in size and shape to the surface of the condensate tub 36 that rests on the floor 28 of the tank 12. Outside air is conducted through the shaft 46 toward the floor 28 of the tank 12 to the area in which the condensate tub 36 rests. Thus, condensate 54 in the condensate tub 36 is cooled. In order to improve heat exchange between the floor 28 and the outside air, a ventilator 48 can be arranged at an air intake of the shaft 46. The ventilator 48 conveys outside air to the floor 28 via a coaxial air path 50 located in the shaft 46. The air then recirculates to the outside again, as is indicated by arrows in FIG. 1, through a ring slot between the shaft 46 and the air path 50, as well as through air outlet vents 52 in the casing 10.

The water tub 30 and the condensate tub 36 are placed in the working space 20. The water tub 30 is then filled with water to form the water supply 32. A hot air ventilator (not shown) in the hot air mantle 18 conveys air upwards along the walls of the tank 12. The heaters 22, 24 heat the working space 20 to the specified regulated temperature, as described above.

The heaters 22 are controlled in a conventional manner in order to heat the water supply 32 and the water tub 30, through the floor 28 of the tank 12, to a temperature which is approximately the same as or slightly higher than the temperature of the working-space 20. Because of heat conductivity of the floor 28, the heaters 22 also heat an area of the floor 28 in which the condensate tub 36 rests. However, this area of the floor 28 is cooled by outside air which is conveyed through the shaft 46 so that the condensate tub 36, which rests in heat-conducting contact with the floor 28, is regulated to a temperature of approximately 3° C. below the temperature of the working space 20. The regulation can vary according to the temperature of the outside air used for cooling. Since the water tub 30 and the condensate tub 36 do not touch, no direct heat exchange between the water tub 30 and the condensate tub 36 takes place. Accordingly, a regulated temperature difference between the water supply 32 and the condensate tub 36 is maintained.

Regulation of the temperature of the working spaces 20 can be provided by a variety of means known to one of ordinary skill in the art. For example, conventional temperature sensing and control circuitry 56 can be coupled to a working space temperature sensor 58, a condensate temperature sensor 60, and an outside air temperature sensor 62. The sensors 58, 60, 62 are of a conventional type used to provide signals that vary according to sensed temperatures. The circuitry 56 is also coupled to the ventilator 48 and provides a signal thereto in order to control the speed of the ventilator 48 in a conventional manner. In that way, the circuitry 56 can cool the condensate tub 36 by varying the speed of the ventilator 48 (to vary the volume of outside air provided thereto) according to the temperatures of the working space 20, the condensate 54 and the outside air.

Since the temperature of the water supply 32 is approximately the same or slightly higher than the temperature of the working space 20, the water from the water tub 30 evaporates relatively rapidly due to the large evaporation surface area of the water supply 32. The evaporation causes a high atmospheric humidity in the working space 20. Since the condensate tub 36 is maintained at a temperature which is lower than the temperature of the working-space 20, the temperature of the condensate tub 36 is below the dew point of the working space so that water vapor in the atmosphere of the working-space 20 tends to condense in the condensate tub 36 to form the condensate water 54. At the same time, the drip rim 40 guarantees that condensate which settles at the edge 36 drips either into the condensate tub 36 or into the water tub 30, and does not reach the floor 28 between the water tub 30 and the condensate tub 36. Condensation of water vapor at the condensate tub 36 dehumidifies the working-space 20 to the point where the temperature of the walls of the tank 12 is reliably above the dew point at all locations within the working space 20. Condensation on the walls of the tank 12 is therefore inhibited. The vapor barrier block which is formed by the tightly locking edge 42 prevents atmosphere of the working space 20, having a high atmospheric humidity, from coming into contact with and leading to condensation in the region of the floor 28 that is cooled by outside air.

While the invention has been disclosed in connection with the preferred embodiments shown and described in detail, various modifications and improvements thereon will become readily apparent to those skilled in the art. Accordingly, the spirit and scope of the present invention is to be limited only by the following claims.

What is claimed is:

1. Incubator, comprising:
    a working space formed inside walls of a tank, said working space having a floor portion;
    a hot air mantle, provided outside the tank in heat conductive contact with the walls, for heating said working space to a predetermined working space temperature;
    a heatable water tub, located inside said working space, said water tub being maintained at a temperature at least substantially equal to the working space temperature in order to generate a high atmospheric humidity within said working space;
    a condensate tub, located inside the working space, said condensate tub having an evaporation surface for receiving condensate and being maintained at a temperature less than the working space temperature; and
    means for maintaining a temperature difference between said heatable water tub and said condensate tub in order to provide a high atmospheric humidity inside said working space while keeping a remainder of said working space relatively free of condensation.

2. Incubator, according to claim 1, wherein at least one of said water tub and said condensate tub are formed in the floor portion.

3. Incubator, according to claim 1, wherein at least one of said water tub and said condensate tub are formed as basins placed on the floor portion in heat conductive contact with the floor portion.

4. Incubator, according to claim 1, wherein said means for maintaining a temperature difference comprises:
    heaters, disposed about the floor portion and at least partially outside the tank, for heating water in said water tub; and
    cooling means, disposed about an outside area of the floor portion, for cooling said condensate tub.

5. Incubator, according to claim 4, further comprising:
means for regulating said cooling means.

6. Incubator, according to claim 2, wherein said means for maintaining a temperature difference comprises:
heaters, disposed about the floor portion and at least partially outside the tank, for heating water in said water tub; and
cooling means, disposed about an outside area of the floor portion, for cooling said condensate tub.

7. Incubator, according to claim 6, further comprising:
means for regulating said cooling means.

8. Incubator, according to claim 3, wherein said means for maintaining a temperature difference comprises:
heaters, disposed about the floor portion and at least partially outside the tank, for heating water in said water tub; and
cooling means, disposed about an outside area of the floor portion, for cooling said condensate tub.

9. Incubator, according to claim 8, further comprising:
means for regulating said cooling means.

10. Incubator, according to claim 4, wherein said cooling means cools said condensate tub by directing a cool air supply from outside the tank.

11. Incubator, according to claim 10, further comprising:
heat insulation disposed outside the tank; and
a shaft, for guiding the cool air supply from outside the incubator past said heat insulation.

12. Incubator, according to claim 11, further comprising:
a ventilator, for directing the cool air supply through said shaft.

13. Incubator, according to claim 12, wherein said ventilator is responsive to temperature of air outside of said incubator.

14. Incubator, according to claim 5, wherein said means for regulating is responsive to temperature of air outside of said incubator.

15. Incubator, according to claim 3, wherein said water tub is separate from and insulated from said condensate tub.

16. Incubator, according to claim 15, wherein said water tub and said condensate tub are independently located on the floor portion.

17. Incubator, according to claim 16, wherein said condensate tub is arranged in an opening of, and is surrounded by, said water tub.

18. Incubator, according to claim 17, wherein said condensate tub includes a drip brim that overlaps an edge of said water tub.

19. Incubator, according to claim 17, wherein said condensate tub has a portion of an edge that fits closely against an edge of said water tub in order to form a vapor block.

20. Incubator, according to claim 18, wherein said condensate tub has a portion of an edge that fits closely against the edge of said water tub in order to form a vapor block.

21. Incubator, according to claim 1, further comprising means for maintaining the condensate at a temperature of approximately 3° C. lower than the working space temperature.

22. Incubator, according to claim 2, further comprising means for maintaining the condensate at a temperature of approximately 3° C. lower than the working space temperature.

23. Incubator, according to claim 3, further comprising means for maintaining the condensate at a temperature of approximately 3° C. lower than the working space temperature.

24. Incubator, according to claim 7, wherein said means for regulating said cooling means further includes means for maintaining the condensate at a temperature of approximately 3° C. lower than the working space temperature.

25. Incubator, according to claim 9, wherein said means for regulating said cooling means further includes means for maintaining the condensate at a temperature of approximately 3° C. lower than the working space temperature.

26. Incubator, according to claim 13, wherein said cooling means further includes means for maintaining the condensate at a temperature of approximately 3° C. lower than the working space temperature.

27. Incubator, according to claim 14, wherein said means for regulating further includes means for maintaining the condensate at a temperature of approximately 3° C. lower than the working space temperature.

28. Incubator, according to claim 18, further including means for maintaining the condensate at a temperature of approximately 3° C. lower than the working space temperature.

29. Incubator, according to claim 19, further including means for maintaining the condensate at a temperature of approximately 3° C. lower than the working space temperature.

30. Incubator, according to claim 20, further including means for maintaining the condensate at a temperature of approximately 3° C. lower than the working space temperature.

31. Incubator, comprising:
a working space formed inside walls of a tank, said working space having a floor portion;
a hot air mantle, provided outside the tank in heat conductive contact with the walls, for heating said working space to a predetermined working space temperature;
a heatable water tub, located inside said working space, said water tub being maintained at a temperature at least substantially equal to the working space temperature in order to generate a high atmospheric humidity within said working space;
a condensate tub, located inside the working space, said condensate tub having an evaporation surface for receiving condensate and being maintained at a temperature less than the working space temperature; and
heaters, disposed about the floor portion and at least partially outside the tank, for heating water in said water tub, which provide a high atmospheric humidity inside said working space while keeping a remainder of said working space relatively free of condensation.

32. Incubator, comprising:
a working space formed inside walls of a tank, said working space having a floor portion;
a hot air mantle, provided outside the tank in heat conductive contact with the walls, for heating said working space to a predetermined working space temperature;
a heatable water tub, located inside said working space, said water tub being maintained at a temperature at least substantially equal to the working space temperature in order to generate a high atmospheric humidity within said working space;
a condensate tub, located inside the working space, said condensate tub having an evaporation surface for receiving condensate and being maintained at a temperature less than the working space temperature; and
a shaft for guiding a cool air supply from outside the tank to said condensate tub, which provides a high atmospheric humidity inside said working space while keeping a remainder of said working space relatively free of condensation.

* * * * *